(12) United States Patent
Matejka

(10) Patent No.: US 9,771,730 B2
(45) Date of Patent: Sep. 26, 2017

(54) DUMPSTER AND PORTABLE TOILET SYSTEM

(71) Applicant: Jeffrey Matejka, Winona, MN (US)

(72) Inventor: Jeffrey Matejka, Winona, MN (US)

(*) Notice: Subject to any disclaimer, the term of this patent is extended or adjusted under 35 U.S.C. 154(b) by 133 days.

(21) Appl. No.: 14/719,070

(22) Filed: May 21, 2015

(65) Prior Publication Data

US 2016/0130827 A1    May 12, 2016

Related U.S. Application Data

(60) Provisional application No. 62/001,109, filed on May 21, 2014.

(51) Int. Cl.
| | |
|---|---|
| *B60P 1/64* | (2006.01) |
| *E04H 1/12* | (2006.01) |
| *B60P 1/28* | (2006.01) |
| *B60R 15/00* | (2006.01) |

(52) U.S. Cl.
CPC ............ *E04H 1/1216* (2013.01); *B60P 1/286* (2013.01); *B60P 1/6409* (2013.01); *B60R 15/00* (2013.01)

(58) Field of Classification Search
CPC ...... B60R 15/04; B65F 1/1426; B65F 1/1452; B65F 2003/006; B65F 2003/008; B60P 1/6427
USPC ..................................................... 4/300, 449
See application file for complete search history.

(56) References Cited

U.S. PATENT DOCUMENTS

| | | | | |
|---|---|---|---|---|
| 3,228,542 | A * | 1/1966 | Achammer | B60P 1/52 414/373 |
| 3,241,859 | A * | 3/1966 | Fuller | B60P 1/6427 280/423.1 |
| 4,615,810 | A | 10/1986 | Conner | |
| 4,957,323 | A * | 9/1990 | Johnson | E03D 7/00 296/24.39 |
| 5,183,293 | A | 2/1993 | Julian | |
| H001477 | H * | 9/1995 | Payne | B65F 1/1426 405/129.57 |
| 5,548,856 | A * | 8/1996 | Julian | B60R 15/04 4/625 |
| 6,723,173 | B1 * | 4/2004 | Golladay | A47K 11/00 134/21 |
| 7,966,675 | B2 * | 6/2011 | Matejka | E04H 1/1216 4/300 |

(Continued)

FOREIGN PATENT DOCUMENTS

GB     2147333 A *  5/1985  ........... E04H 1/1216

*Primary Examiner* — Erin Deery
(74) *Attorney, Agent, or Firm* — Michael A. Bondi; Moss & Barnett

(57) ABSTRACT

A dumpster and portable toilet system that includes a chassis with a dumpster mounted thereto, a portable toilet housing portion and a transportation vehicle. The chassis has an attachment region. The dumpster portion has an enclosure that is adapted for receiving refuse. The portable toilet housing portion is removably attachable to the attachment region to form a dumpster and portable toilet system. The portable toilet housing portion has a recess formed therein that is adapted to receive a portable toilet. The transportation vehicle has a hoist mechanism for placing the dumpster and portable toilet system onto the transportation vehicle and moving the dumpster and portable toilet system off of the transportation vehicle.

14 Claims, 4 Drawing Sheets

(56) References Cited

U.S. PATENT DOCUMENTS

2007/0205055 A1* 9/2007 Renshaw ................. B66F 9/20
187/222
2012/0167297 A1* 7/2012 Poust ..................... B60R 15/04
4/321

* cited by examiner

DUMPSTER AND PORTABLE TOILET SYSTEM

FIELD OF THE INVENTION

This application claims priority to U.S. Provisional Application No. 62/001,109, which was filed on May 21, 2014, the contents of which are incorporated herein by reference.

FIELD OF THE INVENTION

The invention relates generally to a waste collection system. More particularly, the invention relates to a combination dumpster and portable toilet.

BACKGROUND OF THE INVENTION

When performing various construction projects, it is necessary to remove rubbish that is generated during the construction project. One typical way of collecting and removing rubbish is using an elongated dumpster having an open top.

The dumpster is delivered on a truck to the construction project location. The dumpster is then rolled off the truck and placed on the ground. Once the dumpster is filled with rubbish, the dumpster is rolled onto the truck and taken away for disposal.

When performing construction projects, it is typically not possible to use the plumbing facilities. As it is often necessary for workers to use a toilet while working, portable toilets are often delivered to the work site.

In an effort to increase the efficiency of these construction activities a dumpster and portable toilet system was invented, which is described in U.S. Pat. No. 7,966,675, identifies the same inventor as the present application.

SUMMARY OF THE INVENTION

An embodiment of the invention is directed to a method of removing waste. A chassis and a dumpster portion mounted thereto is provided. The chassis includes an attachment region. The dumpster portion has an enclosure that is adapted for receiving refuse. A portable toilet housing portion is provided. The portable toilet housing portion and the dumpster portion mounted to the chassis are transported to a delivery location. The portable toilet housing portion is attached to the attachment region to form a dumpster and portable toilet system. A transportation vehicle having a hoist mechanism is provided.

The dumpster and portable toilet system is delivered to a use location with the transportation vehicle. The dumpster and portable toilet system is moved off of the transportation vehicle with the hoist mechanism. A portable toilet is positioned in the portable toilet housing portion. The portable toilet includes a toilet, a waste collection tank and an enclosure in which the toilet and the waste collection tank are located. Refuse is placed in the dumpster portion. Bodily excrements are collected in the portable toilet. The dumpster and portable toilet system is moved onto the transportation vehicle with the hoist mechanism.

Another embodiment of the invention is directed to a dumpster and portable toilet system that includes a chassis with a dumpster mounted thereto, a portable toilet housing portion and a transportation vehicle. The chassis has an attachment region. The dumpster portion has an enclosure that is adapted for receiving refuse. The portable toilet housing portion is removably attachable to the attachment region to form a dumpster and portable toilet system. The portable toilet housing portion has a recess formed therein that is adapted to receive a portable toilet. The transportation vehicle has a hoist mechanism for placing the dumpster and portable toilet system onto the transportation vehicle and moving the dumpster and portable toilet system off of the transportation vehicle.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
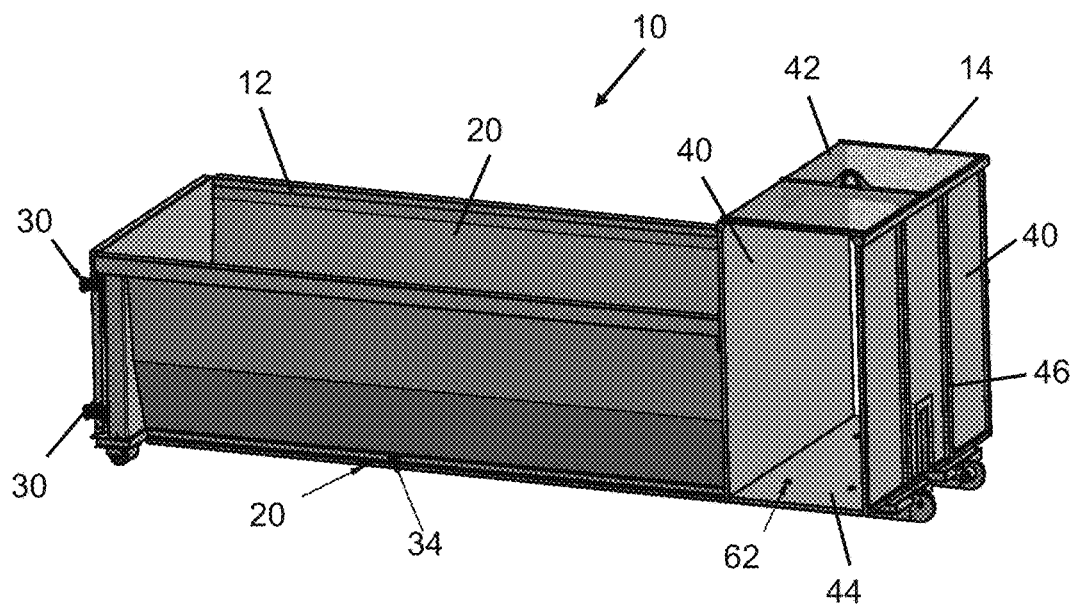
FIG. 1 is an upper perspective view of a dumpster and portable toilet system according to an embodiment of the invention.
Figure 2:
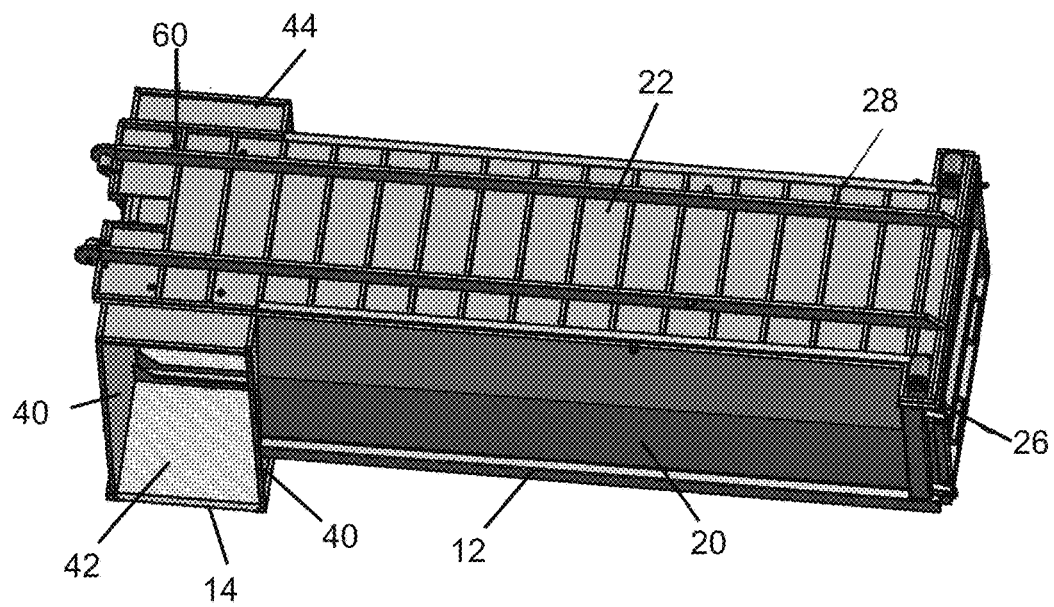
FIG. 2 is a lower perspective view of the dumpster and portable toilet system.
Figure 3:
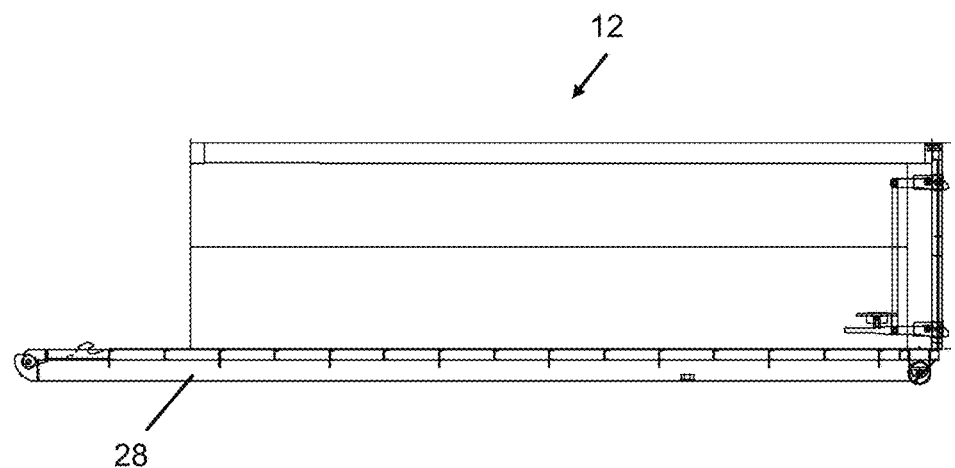
FIG. 3 is a side view of a dumpster portion of the dumpster and portable toilet system.
Figure 4:
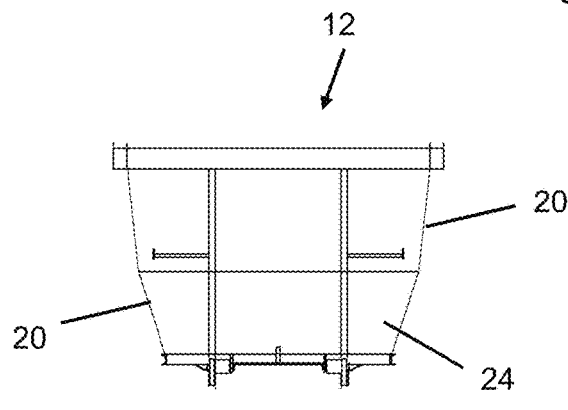
FIG. 4 is a front view of the dumpster portion.
Figure 5:
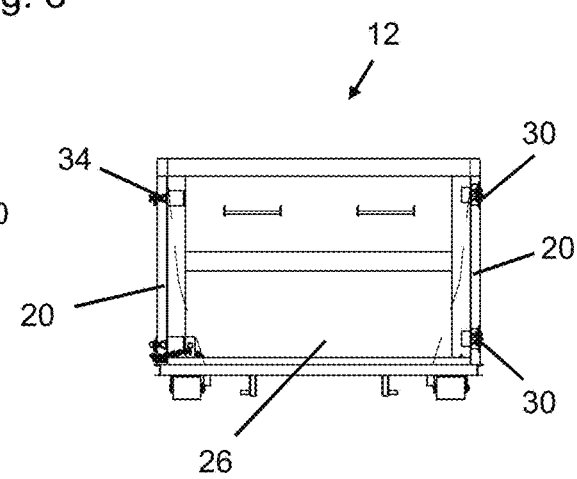
FIG. 5 is a back view of the dumpster portion.

An embodiment of the invention is directed to a dumpster and portable toilet system, as illustrated at 10 in the figures. The dumpster and portable toilet system 10 generally includes a dumpster portion 12 and a portable toilet housing portion 14, as illustrated in FIGS. 1 and 2.

In some configurations, the dumpster portion 12 can be formed with a capacity of about 10 yards, 20 yards or 30 yards. The dumpster portion 12 includes side panels 20, a bottom panel 22, a front panel 24 and a rear panel 26, as illustrated in FIGS. 1-5.

The rear panel 26 may be movable between an open position and a closed position. In certain embodiments, a pair of hinges 30 may be provided to pivotally mount the rear panel 26 with respect to the other parts of the dumpster portion 12. When the rear panel 26 is in a closed configuration, the rear panel 26 substantially closes the rear end of the dumpster portion 12. A lock mechanism 34 may be used to retain the rear panel 26 in the closed configuration.

When the rear panel 26 is in an open configuration, the rear panel 26 may be positioned adjacent to one of the side panels 20 so that the rear end of the dumpster portion 12 is substantially open. The open configuration may facilitate loading and unloading of items in the dumpster portion 20. A retaining mechanism such as a chain may be provided on the dumpster portion 12 to retain the rear panel 26 in the open configuration.

The portable toilet housing portion 14 may include side panels 40, a top panel 42, a bottom panel 44 that define a rectangular enclosure, which is adapted to receive at least one portable toilet 82 as illustrated in FIGS. 1, 2, 6 and 7. In certain embodiments, the rectangular enclosure is adapted to receive two portable toilets that are oriented to face opposite sides of the dumpster and portable toilet system 10. This configuration enables the interiors of the portable toilets to be accessed while the portable toilets are in the portable toilet housing portion 14.

To increase a strength of the portable toilet housing portion 14, at least one reinforcing member 46 may be provided along at least one of the side panels 40 so that the reinforcing member 46 extends between the top panel 42 and the bottom panel 44. At least one reinforcing member 48 may also be provided along the bottom panel 44 so that the reinforcing member 48 extends between the side panels 40.

While it is illustrated that the side panels 40 and the bottom panel 44 are fabricated from a solid sheet of material, it is possible for the side panels 40 and the bottom panels 44 to have alternate configurations such as being formed with a plurality of holes therein similar to the top panel 42. Alternatively, the portable toilet housing portion 14 may be fabricated without the panels covering the framework.

A lift loop 50 may be provided on the portable toilet housing portion 14 to facilitate movement of the portable toilet housing portion 14. The lift loop 50 may be attached to at least one gusset 52 that extends between the side panels 40. The at least one gusset 52 increases the strength of the portable toilet housing portion 14 to thereby reduce the potential of damage to the portable toilet housing portion 14 during the lifting process.

Figures 6, 7:
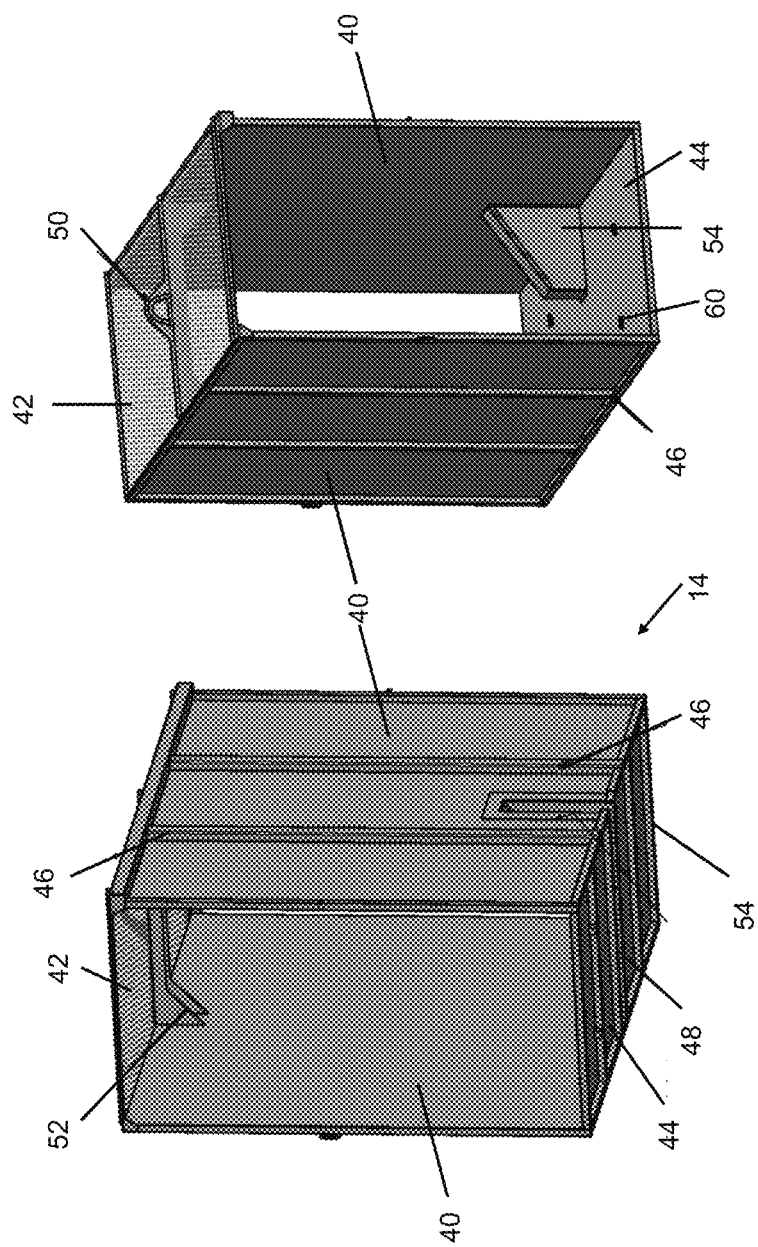
FIG. 6 is an upper perspective view of a portable toilet enclosure of the dumpster and portable toilet system.
FIG. 7 is a lower perspective view of a portable toilet enclosure.
Figure 8:
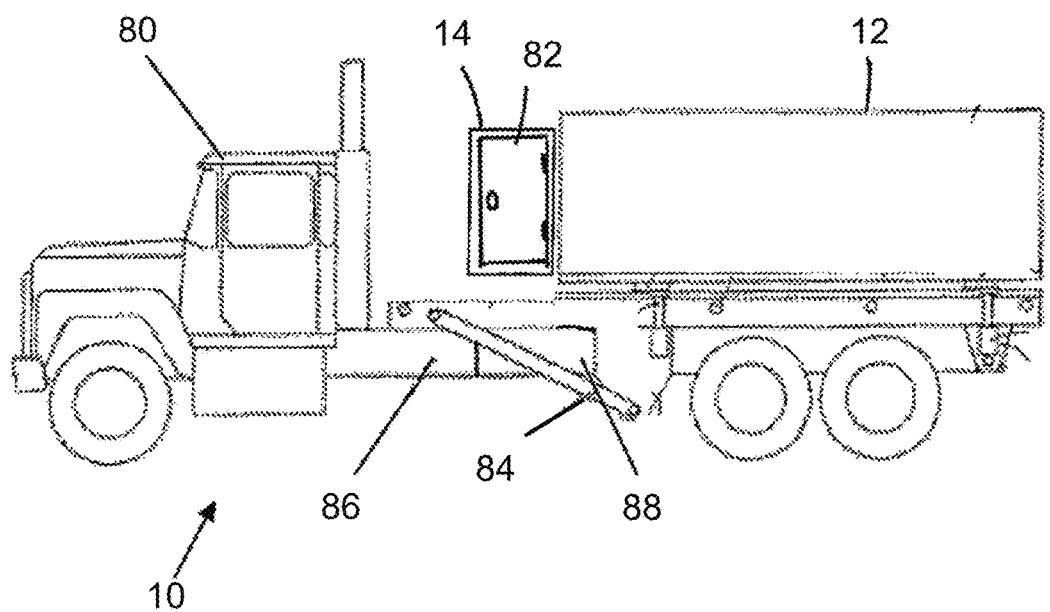
FIG. 8 is a side view of the dumpster and portable toilet system on a transport vehicle.

Depending on the type of hoist mechanism 84 that is provided on the transport vehicle 80, a doghouse recess 54 may extend into the portable toilet housing portion 14 to accommodate a portion of the lift mechanism. A cover may be provided over at least a portion of the doghouse recess 54, as illustrated in FIG. 6. A person of skill in the art will appreciate that the hoist mechanism 84 may assume a variety of configurations, examples of which include a arm (illustrated in FIG. 8).

The portable toilet housing portion 14 is removably attached to the dumpster and portable toilet system 10. Removably attaching the portable toilet housing portion 14 enhances the efficiency at which the dumpster and portable toilet system 10 can be shipped during the manufacturing and distribution process.

In certain embodiments, the bottom panel 22 extends under the location at which it is desired for the portable toilet housing portion 14 to be mounted. The bottom panel 44 of the portable toilet housing portion 14 includes at least one elongated slot 60 formed therein. The elongated slot 60 is adapted to receive a screw 62 that extends through an aperture in the bottom panel 22.

The elongated slot 60 can be oriented generally parallel to a length of the dumpster and portable toilet system 10 from the front and rear ends thereof. The elongated slot 60 thereby enables a position of the portable toilet housing portion 14 to be adjusted with respect to the other portions of the dumpster and portable toilet system 10.

A chassis 28 may be provided on a lower surface thereof to facilitate moving the dumpster and portable toilet system onto and off of a transport vehicle. In certain embodiments, the chassis 28 comprises two rails that are mounted in a spaced-apart configuration. The rails may extend substantially between the front and rear ends of the dumpster and portable toilet system 10. The dumpster and portable toilet system 10 may be equipped with rollers or casters to aid in the positioning and movement of the dumpster and portable toilet system 10.

Portable toilets 82 contained within the toilet housing portion 14 can be secured by locking a chain around the portable toilet housing portion 14, thereby preventing the removal of the portable toilet 82 from the portable toilet housing portion 14. Alternatively, the portable toilet housing portion 14 can be equipped with lock bars (not shown) that span between the side panels 40 and are detachably locked to the portable toilet housing portion 14.

As an alternative to forming the portable toilet 82 separate from the other components of the portable toilet housing portion 14, it is possible that the portable toilet 82 may be integrally fabricated as part of the portable toilet housing portion 14.

In operation, The dumpster and portable toilet system 10 is fabricated with the dumpster portion 12 attached to the chassis 28. This configuration provides the invention with an appearance that is similar to the configuration set forth in FIGS. 3-5. The portable toilet housing portion 14 is fabricated separate from the other aspects of the dumpster and portable toilet system. In this configuration, the portable toilet housing portion 14 has a shape that is similar to illustrated in FIGS. 6 and 7.

The components of dumpster and portable toilet system 10 are shipped to a desired use location such as by placing at least a portion of the portable toilet housing portion 14 in the dumpster portion 12. Alternatively, the portable toilet housing portion 14 may be positioned on its side adjacent to the dumpster portion 12. Using such a configuration reduces the overall height of the components during the shipping and distribution process because a height of the portable toilet housing portion 14 when attached to the chassis may be taller than the dumpster portion 12 as illustrated in FIG. 1.

Because of the reduced overall height of the components in this configuration, it may be possible to stack two of the dumpster and portable toilet systems 10 on top of each other on a conventional flatbed trailer and have the overall height of such a configuration not exceed applicable height regulations such that no special permit is required for the vehicle to travel over most roads.

Once the dumpster and portable toilet system 10 is delivered, the portable toilet housing 14 may be positioned on an attachment region proximate a forward end of the chassis 28 as illustrated in FIGS. 1 and 2 and then attached to the chassis 28 by extending bolts through the elongated slots 60. During the process of positioning the portable toilet housing 14 on the chassis 28, a lifting mechanism (not shown) can utilize the lift loop 50 to facilitate lifting and positioning of the portable toilet housing 14. The dumpster and portable toilet system 10 is then ready for delivery to a location for use.

The dumpster and portable toilet system 10 is placed on the transport vehicle 80 and delivered to the use location. While it is possible to place the portable toilet 82 in the dumpster and portable toilet system 10 after delivery to the use location, the portable toilet 82 is preferably placed in the dumpster and portable toilet system 10 prior to delivery to the use location.

Once at the use location, the dumpster and portable toilet system 10 is moved off of the transport vehicle 80 using the hoist mechanism 84. The fresh liquid pump system is used to place fresh liquid in the portable toilet. The transport vehicle 80 may include a fresh liquid storage tank as well as a pumping system for conveying the fresh liquid from the fresh liquid storage tank to the portable toilet.

The dumpster and portable toilet system 10 is then used by placing refuse in the dumpster portion 20 and using the portable toilet 82 for collection of bodily excrements such as urination and defecation. When done using the dumpster and portable toilet system 10, the transport vehicle 80 returns to the use location.

Prior to placing the dumpster and portable toilet system 10 on the transport vehicle 80 with the hoist mechanism 84, a waste pump 86 may be used to remove waste from the portable toilet 82. The waste pump 86 may be attached to the transport vehicle 80 and cause the waste to be transferred to a waste storage tank on the transport vehicle 80. It is also possible to utilize a cover to prevent the liquid from splashing outside of the designated portion of the portable toilet 82 during the transportation process.

Alternatively, if the portable toilet 82 needs service prior to filling of the dumpster portion 20 with refuse, the waste pump 86 may be used to remove waste from the portable toilet 82 and then the fresh liquid pump 88 may be used to place fresh liquid into the portable toilet 82.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of removing waste comprising:
   providing a chassis and a dumpster portion mounted thereto, wherein the chassis includes an attachment region and wherein the dumpster portion has an enclosure that is adapted for receiving refuse;
   providing a portable toilet housing portion;
   transporting the portable toilet housing portion and the dumpster portion mounted to the chassis to a delivery location, wherein at least a portion of the portable toilet housing portion is placed in the dumpster portion when transporting the portable toilet housing portion and the dumpster portion mounted to the chassis to the delivery location;
   attaching the portable toilet housing portion to the attachment region to form a dumpster and portable toilet system;
   providing a transportation vehicle comprising a hoist mechanism;
   delivering the dumpster and portable toilet system to a use location with the transportation vehicle;
   moving the dumpster and portable toilet system off of the transportation vehicle with the hoist mechanism;
   positioning a portable toilet in the portable toilet housing portion;
   placing refuse in the dumpster portion;
   collecting bodily excrements in the portable toilet; and
   moving the dumpster and portable toilet system onto the transportation vehicle with the hoist mechanism.

2. The method of claim 1, wherein the portable toilet housing portion comprises a frame and panels that substantially cover the frame and wherein the dumpster portion comprises a pair of side panels, a bottom panel, a front end panel, and a back end panel that are attached together to form the enclosure and wherein at least the back end panel is pivotally attached to the dumpster portion.

3. The method of claim 1, wherein the portable toilet housing portion further comprises a lift loop attached thereto.

4. The method of claim 1, wherein a height of the portable toilet housing portion when attached to the attachment region is taller than a height of the dumpster portion.

5. A method of removing waste comprising:
   providing a chassis and a dumpster portion mounted thereto, wherein the chassis includes an attachment region and wherein the dumpster portion has an enclosure that is adapted for receiving refuse;
   providing a portable toilet housing portion, wherein a lower surface of the portable toilet housing portion includes at least one elongated slot formed therein;
   transporting the portable toilet housing portion and the dumpster portion mounted to the chassis to a delivery location;
   attaching the portable toilet housing portion to the attachment region to form a dumpster and portable toilet system by extending a bolt through each of the elongated slots and into the chassis;
   providing a transportation vehicle comprising a hoist mechanism;
   delivering the dumpster and portable toilet system to a use location with the transportation vehicle;
   moving the dumpster and portable toilet system off of the transportation vehicle with the hoist mechanism;
   positioning a portable toilet in the portable toilet housing portion;
   placing refuse in the dumpster portion;
   collecting bodily excrements in the portable toilet; and
   moving the dumpster and portable toilet system onto the transportation vehicle with the hoist mechanism.

6. The method of claim 5, wherein the at least one elongated slot enables a position of the portable toilet housing portion to be adjusted when attaching the portable toilet enclosure to the attachment region.

7. The method of claim 1, and further comprising:
   delivering fresh liquid from a fresh liquid storage tank attached to the transportation vehicle to the portable toilet using a fresh liquid pumping system;
   after bodily excrements are collected in the portable toilet, removing the bodily excrements from the portable toilet; and
   collecting the removed bodily excrement in a waste storage tank attached to the transportation vehicle.

8. A dumpster and portable toilet system comprising:
   a chassis with a dumpster mounted thereto, wherein the chassis has an attachment region and wherein the dumpster portion has an enclosure that is adapted for receiving refuse;
   a portable toilet housing portion that is removably attachable to the attachment region to form a dumpster and portable toilet system, wherein the portable toilet housing portion has a recess formed therein that is adapted to receive a portable toilet, wherein a lower surface of the portable toilet housing portion includes at least one elongated slot formed therein and wherein a bolt is extended through each of the elongated slots and into the chassis when the portable toilet housing portion is attached to the attachment region; and a transportation vehicle comprising a hoist mechanism for placing the dumpster and portable toilet system onto the transportation vehicle and moving the dumpster and portable toilet system off of the transportation vehicle.

9. The dumpster and portable toilet system of claim 8, wherein at least a portion of the portable toilet housing portion is configured to be placed in the dumpster portion when transporting the portable toilet housing portion and the dumpster portion mounted to the chassis to a delivery location.

10. The dumpster and portable toilet system of claim 8, wherein the portable toilet housing portion comprises a frame and panels that substantially cover the frame and wherein the dumpster portion comprises a pair of side panels, a bottom panel, a front end panel, and a back end panel that are attached together to form the enclosure and wherein at least the back end panel is pivotally attached to the dumpster portion.

11. The dumpster and portable toilet system of claim 8, wherein the portable toilet housing portion further comprises a lift loop attached thereto.

12. The dumpster and portable toilet system of claim 8, wherein a height of the portable toilet housing portion when attached to the attachment region is taller than a height of the dumpster portion.

13. The dumpster and portable toilet system of claim 8, wherein the at least one elongated slot enables a position of the portable toilet housing portion to be adjusted when attaching the portable toilet enclosure to the attachment region.

14. The dumpster and portable toilet system of claim 8, wherein a portable toilet is removably mounted in the portable toilet housing portion or integrally fabricated in the portable toilet housing portion.

\* \* \* \* \*